US00PP25009P3

(12) United States Plant Patent
Pinochet

(10) Patent No.: US PP25,009 P3
(45) Date of Patent: Oct. 28, 2014

(54) **VARIETY OF *PRUNUS* ROOTSTOCK NAMED 'APRIDWARF'**

(50) Latin Name: *(Prunus besseyi×P. salicina)×(P. Armeniaca)*
Varietal Denomination: Apridwarf

(75) Inventor: Jorge Pinochet, Barcelona (ES)

(73) Assignee: Agromillora Iberia, S.L., Barcelona (ES)

( * ) Notice: Subject to any disclaimer, the term of this patent is extended or adjusted under 35 U.S.C. 154(b) by 189 days.

(21) Appl. No.: 13/573,434

(22) Filed: Sep. 14, 2012

(65) Prior Publication Data

US 2014/0082779 P1 Mar. 20, 2014

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Wendy C Haas
(74) *Attorney, Agent, or Firm* — The Webb Law Firm

(57) ABSTRACT

A new and distinct hybrid plum-apricot plant used as a rootstock that exhibits root-knot nematode resistance, no suckering, high tolerance to root asphyxia, and high compatibility with apricot varieties.

4 Drawing Sheets

Botanical classification: (*Prunus besseyi×P. salicina*)×(*P. Armeniaca*).

Varietal denomination: 'Apridwarf'.

BACKGROUND OF THE INVENTION

The present invention comprises a new and distinct cultivar of a plum-apricot hybrid (*Prunus besseyi×P. salicina*)×(*P. Armeniaca*) used as a rootstock known by the varietal name 'Apridwarf'. The new variety was discovered in Barcelona, Spain in 1999 as a result of a planned breeding program. The new variety is the result of a cross between the cherry plum cultivar 'Sapalta' (*P. besseyi×P. salicina*) (female parent, unpatented) crossed with an unknown clone of *P. armeniaca* (male parent, unpatented). The purpose of the breeding program was to develop a low vigor rootstock that is well adapted to warm Mediterranean conditions, compatible with apricot varieties, and that has a high tolerance to poorly drained heavy soils that suffer from water logging conditions. The new variety exhibits high resistance to root-knot nematodes, and resistance to several soil-borne fungi, especially *Rosellinia necatrix*. The genotype has low to medium chilling requirements and good productivity. It differs from both parents in its leaf shape and low vigor. Further, the clone does not emit suckers (root and crown) and tolerates water logging conditions better than its plum and apricot parents. It is less sensitive to *Agrobacterium tumefaciens* than both parents and also blooms 7 to 10 days earlier. Additionally, the new variety is similar to 'VVA-1' (U.S. Plant Pat. No. 15,995) (*Prunus tomentosa×P. cerasifera*) by exhibiting good compatibility with apricot varieties, low vigor, and good productivity. However, 'Apridwarf' differs in leaf shape, root-knot nematode resistance, and suckering from 'VVA-1'. The new variety has been field tested and has been found to retain its distinctive characteristics and remain true to type through successive propagations. The following characteristics distinguish 'Apridwarf' from other varieties known to the breeder:

1. Low tree size with a good capacity to control vigor;
2. High tolerance to root asphyxia;

3. Induces fruit precocity (early ripening). Anticipates maturity in all tested apricot varieties when compared with other plum or apricot rootstocks;
4. Resistance to *Rosellinia necatrix* (soil-borne fungus);
5. High resistance to root-knot nematodes (*Meloidogyne* spp.);
6. Does not emit root, nor crown suckers;
7. Induces a sustained production from year to year
8. Compatible with European and Japanese plum varieties; and
9. Chilling requirements within the range of 400 to 600 cu.

DESCRIPTION OF THE DRAWINGS

The accompanying photographic drawings illustrate the new variety with the color being as nearly true as is possible with color illustrations of this type.

DESCRIPTION OF THE PLANT

Figure 1:
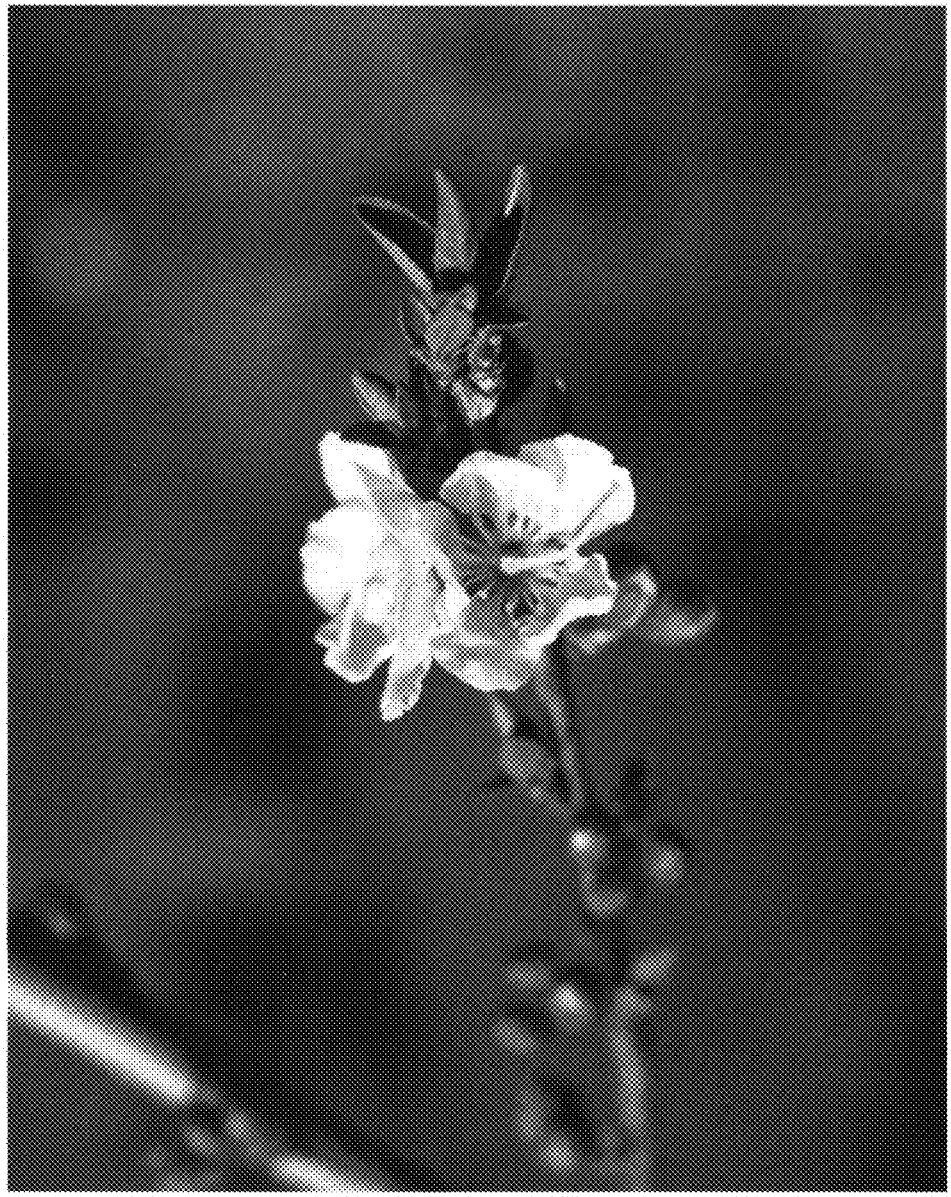
FIG. 1 shows the flowers of the new variety.
Figure 2:
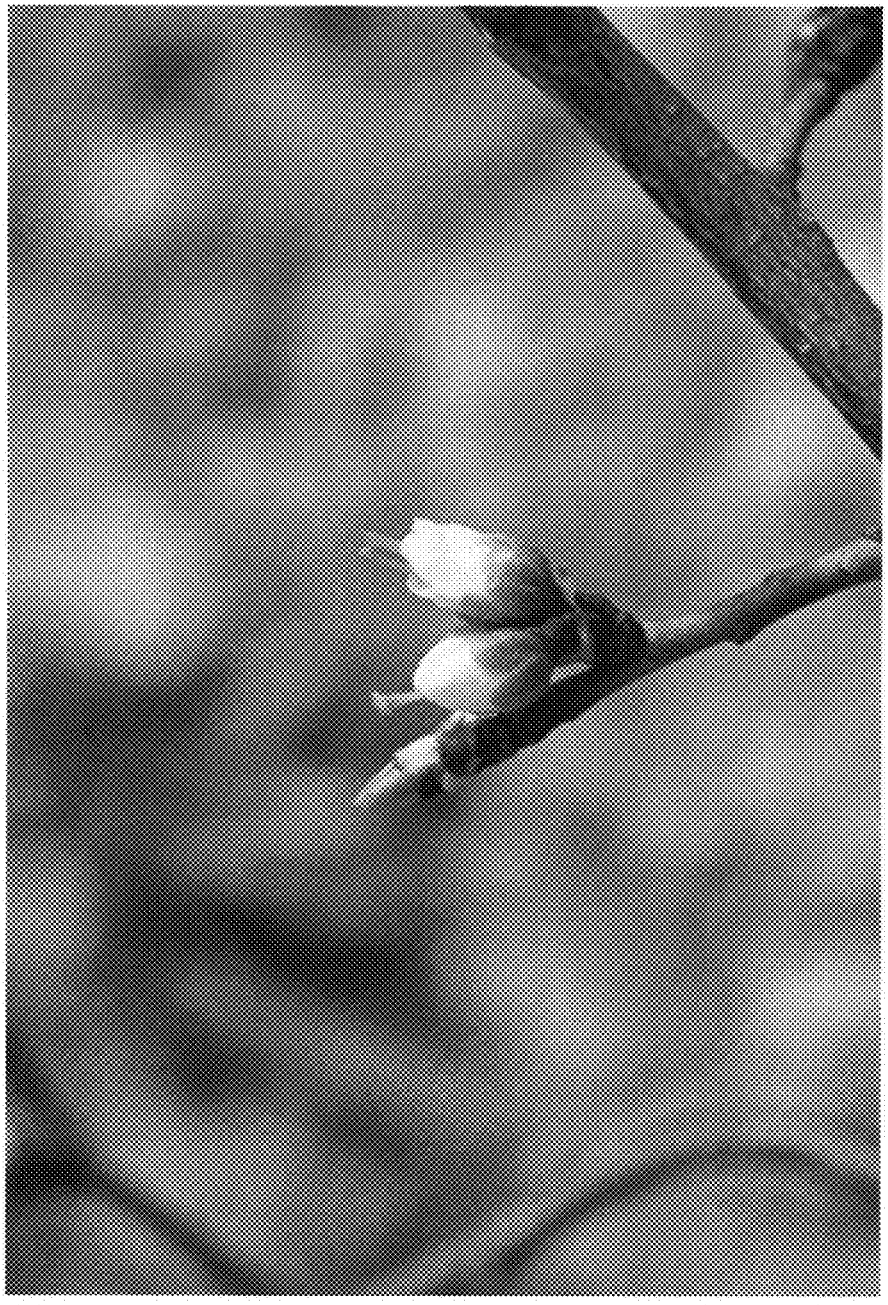
FIG. 2 shows a close-up view of flower buds of the new variety.
Figure 3:
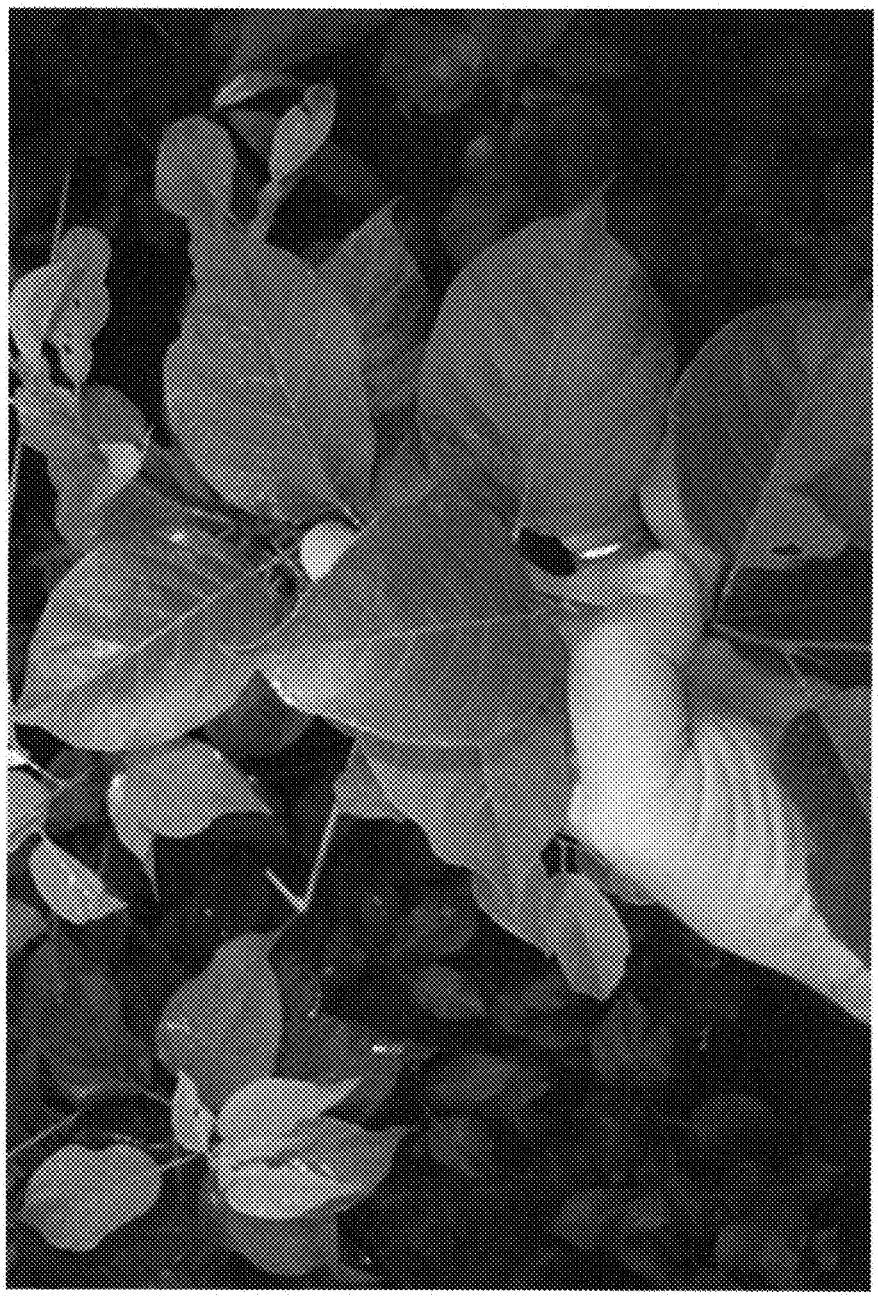
FIG. 3 shows the leaves of the new variety.
Figure 4:
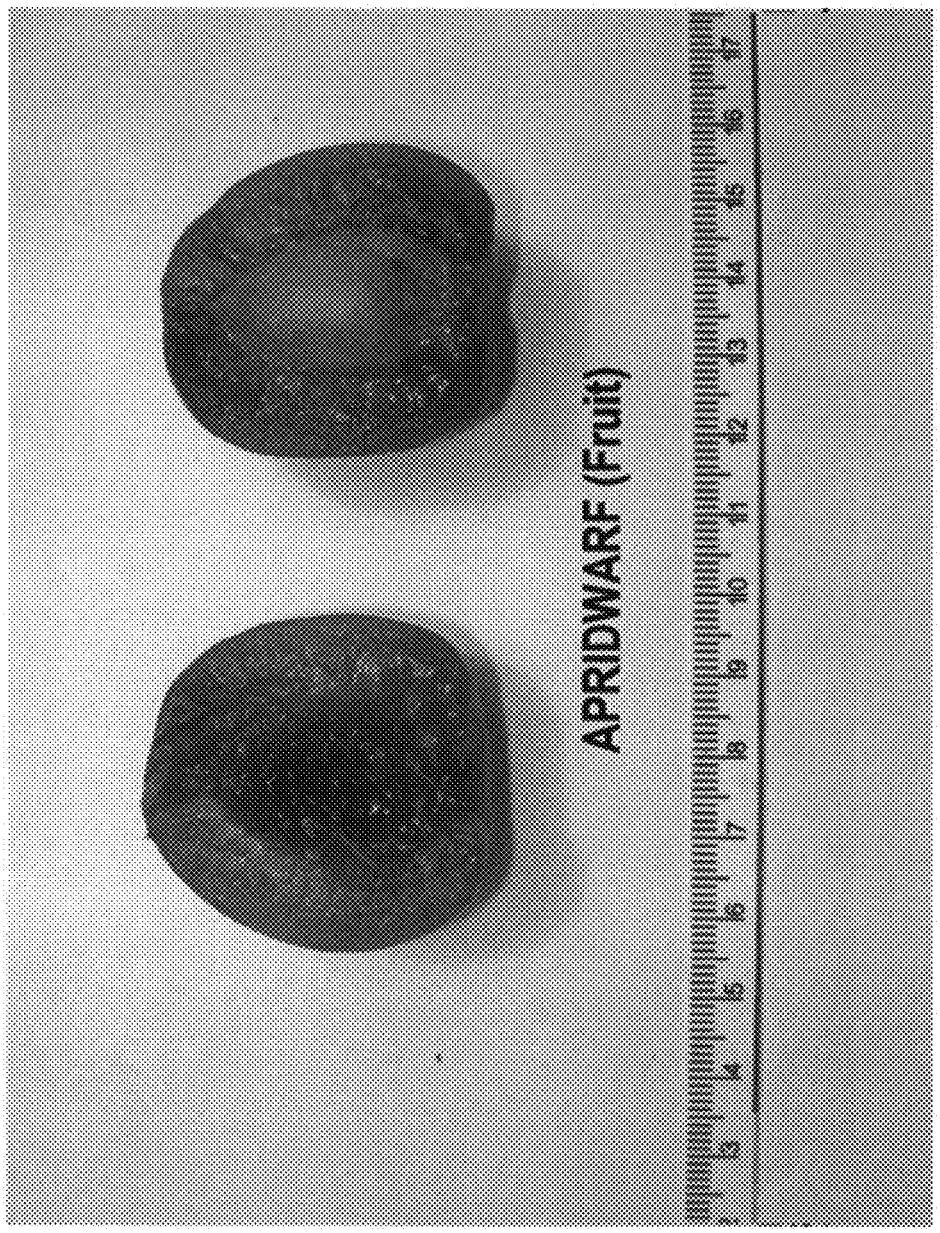
FIG. 4 shows a mature fruit of the new variety.

The following detailed description sets forth the characteristics of the new cultivar. The data which defines these characteristics was collected under natural daylight on plants produced by asexual reproductions via in vitro propagation carried out in Barcelona, Spain in March of 2000. The plants were grown under normal field conditions with drip irrigation and in 40 liter containers. Color designations are presented with reference to the "Dictionary of Color" by A. Maerz and M. Rea Paul, Second Edition (1950).

TREE

Age: 7 years.
Size: 2 meters tall.

Vigor: Low.
Density: Low to medium.
Form: Compact.
Production: Medium to abundant.
Growth type: Upright and spreading.
Bearing: Very scarce fruit bearing.
Pathogen resistance:
*Fungal disease.*—*Rosellinia necatrix.*
*Insects.*—Unknown.
*Mites.*—Unknown.
*Viruses.*—Unknown.
*Other diseases.*—Root-knot nematodes (*Meloidogyne* spp.).
Rootstock performance:
*Root sprouts* (*suckering*).—Not present.
*Anchorage.*—Weak, with a filamentous root system.
*Compatibility.*—Apricot and plum (European and Japanese plum).
*Vigor.*—Low (10-20% less than 'VVA-1').
Trunk:
*Size.*—Perimeter of 21 cm.
*Surface texture.*—Fairly rough with longitudinal scarf-skin and horizontally oriented lenticels.
*Bark color.*—Plate 7, E 7.
*Lenticels.*—Length: 2 to 6 mm. Width: 1 to 1.5 mm. Color: Plate 5, A 1. Density: Medium.
Branches:
*Diameter.*—Variable; from 4 to 7 mm. in the same season.
*Surface texture.*—Smooth in the current season.
*Color.*—Plate 7, E 11 (Trotteur Tan).
*Form.*—Circular in diameter.
*Average angle.*—Acute.
*Bud arrangement.*—Helicoidal throughout the branch.
*Lenticels.*—Length: 1 to 2 mm. in the first year of growth and 2 to 5 mm. in the second year. Width: 0.5 to 1.0 mm. Shape: Younger tissue is initially rounded, turning into elongated horizontally as the branches mature into the season. Density: Medium and increasing as maturity advances. Color: Plate 6, D 7.
Leaves:
*Length.*—6 to 7 cm. (end of season).
*Width.*—4.5 to 5.0 cm.
*Form.*—Broadly oval to rounded.
*Texture.*—Smooth.
*Thickness.*—Medium.
*Base.*—Obtuse and truncated.
*Apex.*—Acute.
*Margin.*—Serrated.
*Pubescence.*—Upper surface: Absent. Lower surface: Absent.
*Color.*—Young leaves: Upper surface: Plate 23, L 8. Lower surface: Plate 22, J 7. Mature leaves: Upper surface: Plate 24, J 6. Lower surface: Plate 23, E 7.
*Petiole.*—Shape: Straight with central groove along the upper side with 2 small nectaries near the base of the leaf. Length: 14 to 17 mm. Diameter: 1 to 1.3 mm. Color: Plate 8, L 9 (Maracaibo).
*Veins.*—Venation type: Tree-type disposition. Color: Upper surface: Plate 7, C 7 (Bonito) changing gradually to Plate 22, I 5 (Sage Green). Lower surface: Plate 7, H 7 (Cedar) changing gradually to light green tones Plate 19, J 6 (Apple Green).
Flower buds:
*Pedicel.*—Length: 1.5 to 3 mm. Diameter: 1.5 to 2 mm. Color: Plate 7, E 9 (Kaffa).
*Bud.*—Length: 2 to 3 mm. Width: 1.5 to 2.5 mm. Shape: Obtuse to rounded. Color: Plate 7, L 9 (Kazak).
Flowers:
*Bloom timing.*—Middle of February to the first week of March in Barcelona, Spain.
*Blooming period.*—10 to 18 days.
*Pollination requirements.*—None.
*Number of flowers per raceme.*—Normally two present.
*Fragrance.*—Not perceptible.
*Petals.*—Number: 5. Length: 6 to 8 mm. Width: 5 to 6 mm. Shape: Rounded. Aspect: Cupped upwards and inwards. Margin: Undulate. Texture and appearance: Smooth.
*Color.*—When opening: Upper surface: Plate 1, A 1. Lower surface: Plate 1, A 1. Fully opened: Upper surface: Plate 2, A 1. Lower surface: Plate 2, A 1.
*Sepals.*—Shape: Rounded. Margin: Slightly serrated. Texture: Pubescence present. Length: 2 to 3 mm. Width: 2 to 2.5 mm. Color: Upper surface: Plate 21, D 4. Lower surface: Plate 20, K 6 (Piquant Green).
*Stamens.*—Number (per flower): 22 to 24. Filament length: 7 to 8 mm.
*Anthers.*—Shape: Kidney-shaped. Length: 1 to 1.3 mm. Color: Plate 12, I 2 (Hay).
*Pollen.*—Color: Plate 12, J 5 (Light Stone). Amount (generally): Abundant.
*Pistils.*—Length: 12 to 14 mm.
*Style.*—Length: 9 to 10 mm. Color: Plate 19, A 1.
*Stigma.*—Shape: Rounded. Color: Plate 12, H 1.
Fruit:
*Size.*—Medium.
*Diameter.*—3.5 to 3.8 cm.
*Length.*—3.9 to 4.1 cm.
*Skin.*—Thickness: Thin. Texture: Pubescent, but very smooth. Tendency to crack: None. Color: Plate 8, H 5 (Chippendale). Ground color: Plate 7, J 8 (Domingo).
*Flesh.*—Aroma: None perceptible. Color: Plate 7, L 7 (Maroon). Texture: Plum-like (Japanese plums). Eating quality: Bitter and acidic.
*Seeds.*—Number per fruit: 1. Length: 3 cm. Breadth: 1.8 cm. Form: Elliptic. Color: Plate 12, H 6 (Roe).
*Stem.*—Length: Variable, but can be long. Width: 3 to 5 mm. Color: Plate 7, J 9 (Tanagra), turning into tones of grey as maturity advances in the season.
Use: As a low vigor rootstock that is highly compatible with apricots, but can also be used for plums.
Tree winter hardiness: Hardy (under the conditions in Spain).
Chill requirements: Low to medium, around 400 to 600 cu (chill units).
Productivity: Steady from year to year. Good fruit yields with anticipated fruit maturity.
Tolerance to root asphyxia: Highly tolerant.
Drought tolerance: Moderately tolerant.
Disease resistance: Highly resistant to root-knot nematodes.

I claim:

1. A new and distinct variety of hybrid plum-apricot plant, as illustrated and described herein.

* * * * *